United States Patent [19]

Koerwer

[11] 4,351,666

[45] Sep. 28, 1982

[54] ENOL DERIVATIVES OF 2-ARYL-1,3-CYCLOHEXANEDIONE COMPOUND AS SUGAR ENHANCER FOR PLANTS

[75] Inventor: John F. Koerwer, Perkasie, Pa.

[73] Assignee: Union Carbide Corporation, Danbury, Conn.

[21] Appl. No.: 163,632

[22] Filed: Jun. 27, 1980

[51] Int. Cl.³ .................... A01N 37/02; A01N 37/06; A01N 31/06; A01N 35/06

[52] U.S. Cl. .......................................... 71/106; 71/76; 71/105; 71/122; 71/123

[58] Field of Search .................. 71/122, 106, 105, 123, 71/76

[56] References Cited

U.S. PATENT DOCUMENTS 4,209,532  6/1980  Wheeler .............................. 71/105

FOREIGN PATENT DOCUMENTS 7009285  1/1971  Netherlands .

Primary Examiner—Catherine L. Mills
Attorney, Agent, or Firm—John A. Shedden; W. Dickheiser; D. Carlson

[57] ABSTRACT

A method for increasing the sugar content of plants by applying to such plants an effective amount of an enol derivative of 2-aryl-1,3-cyclohexanedione compound.

10 Claims, No Drawings

ENOL DERIVATIVES OF 2-ARYL-1,3-CYCLOHEXANEDIONE COMPOUND AS SUGAR ENHANCER FOR PLANTS

FIELD OF THE INVENTION

This invention relates to a novel method for increasing the sugar content of plants by applying to such plants an effective amount of enol derivative of 2-aryl-1,3-cyclohexan dione compound.

BACKGROUND OF THE INVENTION

Certain 2-aryl-1,3-cyclohexanedione compounds are known in the art. For example, U.S. Pat. No. 4,209,532 discloses 2-aryl-1,3-cyclohexanedione compounds and alkali metal and ammonium salts thereof as being useful as miticide, mite ovicides, post-emergent herbicides and pre-emergent herbicides. Likewise, U.S. application Ser. No. 945,005 disclosed enol derivatives of 2-aryl-1,3-cyclohexanedione compounds having herbicidal and scaricidal activity. In addition, U.S. application Ser. No. 781,781 discloses 2- aryl-1,3-cyclohexanedione enol ester compounds as having pre-emergent herbicidal and mite ovicidal activity.

None of the above patent applications discloses the use of 2-aryl-1,3-cyclohexandione compounds to increase the sugar content of plants such as sugar cane (*Saccharum officinerum*) or sorghum (*Sorghum vulgare*). Increased sugar content, of course, increases the value of such plant.

SUMMARY OF THE INVENTION

In accordance with the present invention, it has now been discovered that certain enol derivatives of 2-aryl-1,3-cyclohexanedione compounds can be employed to increase the sugar content of plants, preferably when applied to such plants from one to seven weeks prior to harvesting and in an amount insufficient to exert a herbicidal effect. As a result, an earlier accumulation and significant increase in the sugar content of plants such as sugar cane (*Saccharum officinerum*) and sorghum (*Sorghum vulgare*) can be effected. The resulting plants are of greater commercial walue than the untreated plans.

DETAILED DESCRIPTION OF THE INVENTION

The enol derivatives of 2-aryl-1,3-cyclohexanedione compounds useful as plant sugar enhancers in accordance with the present invention are represented by the formula:

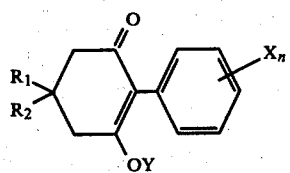

Wherein:
$R_1$ is a hydrogen atom or an alkyl group having from 1 to 4 carbon atoms, $R_2$ is a hydrogen atom, an alkyl group having from 1 to 10 carbon atoms, or a cycloalkyl group having from 5 to 10 carbon atoms.

Y is a hydrogen atom, an alkanoyl, alkynol, alyoyl or alkenoyl group having from 6 to 12 carbon atoms, or a cation.

X is an alkyl group having from 1 to 4 carbon atoms, an alkoxy group having from 1 to 4 carbon atoms, a halogen atoms, or a nitro, amino or cyano group.

n is an integer of 1 to 3.

Preferred compounds within the scope of the above formula include the $C_2$ to $C_{12}$ esters of 3-hydroxy-5-isopropyl-2-(2,4-dimethylphenyl)-2-cyclohexane-1-one and of 3-hydroxy-5-isopropyl-2-(2,4,6-trimethylphenyl)-2-cyclohexen-1-one.

The carbon content of terms $R_1$, $R_2$, Y, and X is limited in that these groups should contain no more than 20 carbon atoms each, preferably no more than 7 carbon atoms. There are generally no more than 3 "X" substituents on the 2-aryl ring, preferably no more than 2 substituents. The X substituents are each individually selected from the group consisting of alkyl, alkoxy, halogen, amino, cyano and nitro groups. When X is an alkyl group in the above formula, it can be either straight or branched chain, e.g., methyl, ethyl, ispropyl, tert-butyl, and the like, and may be substituted with one or more of a variety of substituents, such as halogen or hydroxyl. When X is halogen or is substituted with halogen, the preferred halogen is chlorine. When X is an alkoxy group, it can be straight chain or branch chain, e.g., methoxy, ethoxy, isopropxy, tert-butoxy and the like, and it may be substituted with one or more of a variety of substituents, such as halogen or hydroxyl. When $R_1$ is an alkyl group in the above formula, it can be either straight chain or branched chain, e.g., methyl, ethyl, isopropyl, tert-butyl, and the like, and may be substituted with one or more of a variety of substituents, such as halogen (preferably chlorine) or hydroxyl. When $R_2$ is an alkyl group, it can be either straight or branched chain, e.g., methyl, isopropyl, monyl, decyl, and the like, or it can be a cycloalkyl group such as cyclopentyl, cyclohexyl, and the like, which may be substituted with substituents such as halogen or hydroxyl.

When Y is an alkanoyl group in the above formula, it can be either straight or branched chain, e.g., ethanoyl, isopropanoyl, to decanoyl, and the like, and may be substituted with one or more substituents such as halogen or hydroxyl. When U is aryloyl, it can be any such group having from 6 to 12 carbon atoms, such as benzyloyl. When Y represents a cation in the formula, it is preferably an ammonium radical, an alkaline metal cation, or an alkaline earth metal cation, but it can be any other agriculturally acceptable cation.

The enol derivatives of 2-aryl-1,3-cyclohexanedione compounds employed in the present invention are known compounds and can be prepared by conventional synthesis methods well-known to those skilled in the art. The preparation of such compound is disclosed, for example, in U.S. Pat. No. 4,209,532, incorporated herein by reference.

The compounds employed as plant sugar enhancers in the method of this invention are preferably applied to the plants from 1 to 7 weeks prior to harvesting, more preferably from 3 to 5 weeks prior to harvesting. Such compounds should be applied in an "effective amount", i.e. an amount sufficient to increase the sugar content of the plants. As mentioned above, however, the amount preferably should be insufficient to exert a herbicidal effect on the plant. The proper amount is determined by, and dependent upon, such factors as the particular compound and formulation employed, the method of application, the nature of the plant species to which the compound is being applied, state and condition of the growth of the plant, and the climactic conditions in the area where the compound is being employed. Generally, from about ⅛ to about 8 lb. per acre, preferably from about ⅛ lb. to about 2 lb. per acre, more preferably from about ¼ lb. per acre to about 1 lb. per acre, of the compound is employed.

The enol derivatives of 2-aryl-1,3-cyclohexanedione compounds employed in the method of this invention can be applied to mature plants in a suitable form, e.g. as solutions, emulsions, suspensions, dust formulations, and the like. Such compositions generally contain the active compound in an amount of from about 0.06% by weight to about 26% by weight preferably from about 0.6% by weight to about 1.2% by weight. Both liquid compositions and dust formulations may be conveniently applied from either a ground rig or from an aircraft.

A convenient labratory carrier for the active compounds employed in the method of this invention is water or a mixture of water and acetone. When the compound is water soluble, it can be simply dissolved in amount of water sufficient to give the desired concentration and sprayed on the plants. If desired, a suitable wetting agent may be added to the solution to improve wetting of the foliage and to increase the penetration of the solution into the tissue of the plant. Preferred wetting agents include anionic or nonionic surfactants such as sodium alkyl sulfates, sodium alkyl benzene sulfonates, sodium lignin sulfonates, polyoxyethylene laurel ethers, polyoxyethylene alkyl aryl ethers, polyoxyethylene fatty acid esters, and polyoxyethylene sorbitan fatty acid esters. Such wetting agents generally do not exceed 1% by volume of the final spray solution, and preferably are present in an amount of about 0.1% to about 0.5%, based on the final spray volume.

Those compounds of the present invention which are not sufficiently water-soluble for conventional formulation into aqueous solutions can be prepared as liquid emulsions by dissolving the compounds in a small amount of agriculturally acceptable solvent and then adding an emulsifier and water. Suitable solvents include acetone, n-hexane, toluene, xylene, naptha, isophorone, dimethylformamide, and the like. Hydrocarbon oils, including paraffin oils, aromatic oils, and asphaltic oils can also be employed, although highly aromatic oils are preferred, particularly highly aromatic petroleum-base oils. Suitable emulsifiers include, sodium-2,2'-dinaphthylmethane-6,6'disulfonate, sodium-dibutylsulfonate and sodium oleomethyllaurate.

Alternatively, these compounds may be formulated into variable powders which can be dispersed in water by compounding them with conventional excipients such as fillers, wetting agents, dispersing agents and the like. The wetting agents and emulsifiers mentioned above can be employed in this application. Suitable fillers include vermiculite, attaclay, talc, diatomateous earth, pyrophillite, kaolin, bentonite and the like.

If desired, the active compounds employed in the method of this invention can be compounded with finely-divided, solid excipients, such as those named above, and applied to the plant as a dust formulation.

If desired, two or more compounds of the present invention can be employed in admixture in the method of the present invention. Should such an admixture be used, there is no prescribed ratio in which each particular compound must be present. The concentration of the admixture need only be within the concentration range given above for a single compound, and the rate of application of the admixture should be within the range prescribed above.

The following compounds are illustrative of compounds in the purview of the present invention, all of which can be conveniently prepared by the processes of this invention simply by selecting appropriate reactants and using the procedures described herein to make the $C_2$ to $C_{12}$ enol esters of the following 2-(2'Methyl-4',6'dichlorophenyl)-5,5-dimethyl-1,3-cyclohexanedione 2-(2'-Nitro-4',6'-dibromophenyl)-5,5-dimethyl-1,3-cyclo-hexanedione 2-(2'-Chloro-4'-methoxyphenyl)-5,5-dimethyl,-1,3-cyclo-hexanedione 2-(2'-Methyl-4'-cyanophenyl)-5,5-dimethyl-1,3cyclo-hexanedione 2-(2'-Methyl-4'-trifluoromethylphenyl)-5,5-dimethyl-1,3-cyclohexanedione 2-(2'-Trifluoromethyl-4'-methoxyphenyl)-5,5-dimethyl-1,3-cyclohexanedione 2-(2'-Trifluoromethyl-4'-chlorophenyl)-5,5-dimethyl-1,3-cyclohexanedione 2-(2'-Trifluoromethyl-4'-cyanophenyl)-5,5-dimethyl-1,3-cyclohexanedione 2-(2'-Nitro-3'-methylthio-6'-trichloromethylphenyl)-5,5-dimethyl-1,3-cyclohexanedione 2-(2'-Chloro-4'-nitro-6'-cyanophenyl)-5-150 propyl,3-cyclohexanedione 2-(2'-Chloro-6'-methoxy-4'nitrophenyl)-5,5-dimethyl-1,3-cyclohexanedione 2(2'-Chloro-6'-cyano-4'nitrophenyl)-5,5-dimethyl-1,3-cyclohexanedione 2-(2'-Bromo-4'-aminophenyl)-5,5-dimethyl-1,3-cyclohexanedione 2-(2',6'-Dibromophenyl)-5,5-dimethyl-1,3-cyclohexanedione 2-(2'Methyl-6'-cyano-5'nitrophenyl)-5,5-dimethyl-1,3-cyclohexanedione The following examples are provided in order to illustrate, but in no way limit, the present invention.

EXAMPLES 1 TO 123

A series of compounds as given in Table 1 were applied, one at a time, to sweet sorghum at the two to four leaf stage of growth at a rate in pounds per acre as specified in Table 1. Application was made by spraying 10 ml. of an aqueous solution of each compound in acetone and deionized water upon 25-30 stalks of sorghum (at a volume of 100 gallons per acre). The solution was prepared by mixing each compound in acetone and diluting the resulting mixture with water to a final volume of 10 ml.

The sorghum was harvested two weeks after such treatment. The sap of each stalk was then analyzed for for brix by means of a refractometer, and the findings were compared to untreated control plants, the results being expressed in terms of percent increase in sugar (example vs. control) as given in Table I which follows:

The compounds given in Table I are represented by the following structure:

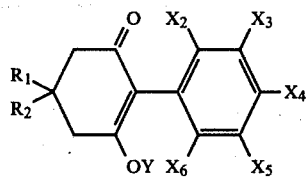

TABLE I

| Example No. | $R_1$ | $R_2$ | Y | $X_2$ | $X_3$ | $X_4$ | $X_5$ | $X_6$ | RATE LBS/A | % INCREASE IN SUGAR |
|---|---|---|---|---|---|---|---|---|---|---|
| 1 | $CH_3$ | $CH_3$ | $-\overset{O}{\underset{\|}{C}}-C_4H_9$ | — | — | $NO_2$ | — | — | 8 | 20 |
| 2 | $CH_3$ | $CH_3$ | $-\overset{O}{\underset{\|}{C}}-CH_3$ | CL | — | — | — | — | 8 | 180 |
| 3 | $CH_3$ | $CH_3$ | $-\overset{O}{\underset{\|}{C}}-C_5H_6$ | CL | — | CL | — | — | 8 | 44 |
| 4 | $CH_3$ | $CH_3$ | $-\overset{O}{\underset{\|}{C}}-C$ | $CH_3$ | — | $CH_3$ | — | — | 8 | 236 |
| 5 | $CH_3$ | $CH_3$ | $-\overset{O}{\underset{\|}{C}}C_2H_4\overset{O}{\underset{\|}{C}}OCH_3$ | $CH_3$ | — | $CH_3$ | — | — | 8 | 236 |
| 6 | $CH_3$ | $CH_3$ | $-\overset{O}{\underset{\|}{C}}-C_6H_{12}CL$ | $CH_3$ | — | $CH_3$ | — | — | 8 | 148 |
| 7 | $CH_3$ | — | $-\overset{O}{\underset{\|}{C}}-CH\overset{C_4H_9}{\underset{C_2H_5}{<}}$ | $CH_3$ | — | $CH_3$ | — | — | 8 | 172 |
| 8 | $CH_3$ | $CH_3$ | $-\overset{O}{\underset{\|}{C}}-CH\overset{C_4H_9}{\underset{C_2H_5}{<}}$ | $CH_3$ | — | $CH_3$ | — | — | 8 | 140 |
| 9 | $CH_3$ | $CH_3$ | $-\overset{O}{\underset{\|}{C}}-CH_3$ | CL | — | CL | — | — | 8 | 60 |
| 10 | $CH_3$ | $CH_3$ | $-\overset{O}{\underset{\|}{C}}-C_5H_{11}$ | $CH_3$ | — | — | — | — | 8 | 396 |
| 11 | $CH_3$ | $CH_3$ | $-\overset{O}{\underset{\|}{C}}-CH\overset{CH_3}{\underset{CH_3}{<}}$ | $CH_3$ | — | $CH_3$ | — | — | 8 | 252 |
| 12 | $CH_3$ | $CH_3$ | $-\overset{O}{\underset{\|}{C}}-C_6H_5$ | $CH_3$ | — | $CH_3$ | — | — | 8 | 148 |
| 13 | $CH_3$ | $CH_3$ | $-\overset{O}{\underset{\|}{C}}-CH_3$ | $CH_3$ | — | $CH_3$ | — | — | 8 | 324 |
| 14 | $CH_3$ | $C_2H_5$ | $-\overset{O}{\underset{\|}{C}}-C_6H_5$ | $CH_3$ | — | — | — | — | 8 | 116 |
| 15 | $CH_3$ | $CH_3$ | $-\overset{O}{\underset{\|}{C}}-CH_3$ | $CH_3$ | — | — | — | — | 8 | 252 |

TABLE I-continued

| Example No. | $R_1$ | $R_2$ | Y | $X_2$ | $X_3$ | $X_4$ | $X_5$ | $X_6$ | RATE LBS/A | % INCREASE IN SUGAR |
|---|---|---|---|---|---|---|---|---|---|---|
| 16 | $CH_3$ | $CH_3$ | $-\overset{O}{\underset{\|}{C}}-C_5H_{11}$ | $CH_3$ | — | $CH_3$ | — | — | 8 | 324 |
| 17 | $CH_3$ | $CH_3$ | $-\overset{O}{\underset{\|}{C}}-CH\overset{C_4H_9}{\underset{C_2H_5}{}}$ | — | — | $CH_3$ | — | — | 8 | 33 |
| 18 | $CH_3$ | $-C_6H_5$ | $-\overset{O}{\underset{\|}{C}}-C_2H_5$ | $CH_3$ | — | $CH_3$ | — | — | 8 | 13 |
| 19 | $CH_3$ | $CH_3$ | $-\overset{O}{\underset{\|}{C}}-CH_3$ | $C_2H_5$ | — | — | — | — | 8 | 67 |
| 20 | $CH_3$ | $CH_3$ | $-\overset{O}{\underset{\|}{C}}-CH_3$ | — | — | — | — | — | 9 | 0 |
| 21 | $CH_3$ | $CH_3$ | $-\overset{O}{\underset{\|}{C}}-CH(CH_3)_2$ | — | — | — | — | — | 8 | 0 |
| 22 | $CH_3$ | $CH_3$ | $-\overset{O}{\underset{\|}{C}}-CH(CH_3)_2$ | — | — | $CH_3$ | — | — | 8 | 60 |
| 23 | $CH_3$ | $CH_3$ | $-\overset{O}{\underset{\|}{C}}-CH(CH_3)_2$ | — | $CH_3$ | $CH_3$ | — | — | 8 | 0 |
| 24 | $CH$ | $CH$ | $-\overset{O}{\underset{\|}{C}}-\overset{CH_3}{\underset{CH_3}{C}}-CH$ | — | — | $CH_3$ | — | — | 8 | 0 |
| 25 | $C_2H_5$ | $C_2H_5$ | $-\overset{O}{\underset{\|}{C}}-CH\overset{C_4H_9}{\underset{C_2H_5}{}}$ | $CH_3$ | — | $CH_3$ | — | — | 8 | 80 |
| 26 | $C_2H_5$ | $C_2H_5$ | $-\overset{O}{\underset{\|}{C}}-C_5H_{11}$ | $CH_3$ | — | $CH_3$ | — | — | 1 | 38 |
| 27 | $C_2H_5$ | $C_2H_5$ | $-\overset{O}{\underset{\|}{C}}-C_9H_{19}$ | $CH_3$ | — | $CH_3$ | — | — | 8 | 87 |
| 28 | $CH_3$ | $CH_3$ | $-\overset{O}{\underset{\|}{C}}-CH(C_4H_9)(C_2H_5)$ | $CH_3$ | — | $CH_3$ | — | $CH_3$ | 8 | 100 |
| 29 | $C_2H_5$ | $C_2H_5$ | $-\overset{O}{\underset{\|}{C}}-CH_3$ | $CH_3$ | — | $CH_3$ | — | — | 8 | 55 |
| 30 | $CH_3$ | $CH_3$ | $-\overset{O}{\underset{\|}{C}}-C_5H_{11}$ | $C_2H_5$ | — | — | — | — | 8 | 119 |
| 31 | $CH_3$ | $CH_3$ | $\overset{O}{\underset{\|}{C}}-C_3H_7$ | $C_2H_5$ | — | — | — | — | 8 | 105 |
| 32 | $CH_3$ | $CH_3$ | $\overset{O}{\underset{\|}{C}}-C_7H_{15}$ | $C_2H_5$ | — | — | — | — | 8 | 119 |

TABLE I-continued
| Example No. | R₁ | R₂ | Y | X₂ | X₃ | X₄ | X₅ | X₆ | RATE LBS/A | % INCREASE IN SUGAR |
|---|---|---|---|---|---|---|---|---|---|---|
| 33 | CH₃ | CH₃ |  | CH₃ | — | CH₃ | — | — | 8 | 105 |
| 34 | CH₃ | CH₃ | 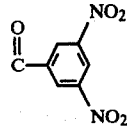 | CH₃ | — | CH₃ | — | — | 8 | 120 |
| 35 | CH₃ | C₂H₅ | 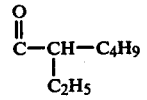 | CH₃ | — | CH₃ | — | — | 8 | 63 |
| 36 | CH₃ | C₂H₅ | 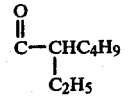 | CL | — | — | — | — | 8 | 133 |
| 37 | CH₃ | C₂H₅ | 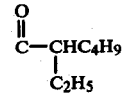 | CL | — | — | — | — | 8 | 133 |
| 38 | CH₃ | C₂H₅ | 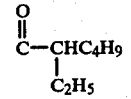 | CH₃ | — | — | — | — | 8 | 37 |
| 39 | CH₃ | |  | CL | — | — | — | — | 8 | 48 |
| 40 | CH₃ | CH₃ | 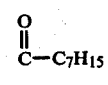 | CL | — | CL | — | — | 8 | 29 |
| 41 |  | — |  | CH₃ | — | CH₃ | — | — | 8 | 148 |
| 42 |  | — | 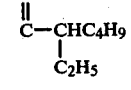 | CH₃ | — | CH₃ | — | — | 8 | 11 |
| 43 |  | —CH₃ |  | CH₃ | — | CH₃ | — | — | 8 | 81 |
| 44 |  | —CH₃ | 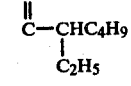 | CH₃ | — | CH₃ | — | — | 8 | 0 |
| 45 |  | —CH₃ | 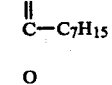 | CH₃ | — | CH₃ | — | — | 8 | 50 |
| 46 |  | —CH₃ |  | CH₃ | — | CH₃ | — | — | 8 | 19 |
| 47 | —CH₃ | —CH₃ |  | CL | — | CL | — | — | 8 | 54 |
| 48 | CH₃ | CH₃ |  | CL | | CL | — | — | 8 | 43 |

TABLE I-continued

| Example No. | $R_1$ | $R_2$ | Y | $X_2$ | $X_3$ | $X_4$ | $X_5$ | $X_6$ | RATE LBS/A | % INCREASE IN SUGAR |
|---|---|---|---|---|---|---|---|---|---|---|
| 49 | $CH_3$ | $CH_3$ | $\overset{O}{\underset{\|}{C}}-C_6H_5$ | $CH_3$ | — | — | — | — | 8 | 129 |
| 50 | $CH_3$ | $C_3H_7$ | $\overset{O}{\underset{\|}{C}}-C_6H_5$ | $CH_3$ | — | $CH_3$ | — | — | 9 | 154 |
| 51 | $CH_3$ | $CH_3$ | $\overset{O}{\underset{\|}{C}}-C_4H_8\overset{O}{\underset{\|}{C}}C_2H_5$ | CL | — | CL | — | — | 8 | 73 |
| 52 | $CH_3$ | $C_3H_7$ | $\overset{O}{\underset{\|}{C}}-\underset{\underset{C_2H_5}{\|}}{CH}C_4H_9$ | $CH_3$ | — | $CH_3$ | — | — | 8 | 91 |
| 53 | $CH_3$ | $C_3H_7$ | $\overset{O}{\underset{\|}{C}}C_5H_{11}$ | $CH_3$ | — | $CH_3$ | — | — | 8 | 146 |
| 54 | $CH_3$ | $C_3H_7$ | $\overset{O}{\underset{\|}{C}}-C_9H_{19}$ | $CH_3$ | — | $CH_3$ | — | — | 8 | 122 |
| 55 | $CH_3$ | $CH_3$ | $\overset{O}{\underset{\|}{C}}-C_{15}H_{31}$ | CH | — | — | — | — | 8 | 11 |
| 56 | $CH_3$ | $CH_3$ | $\overset{O}{\underset{\|}{C}}-CH(C_2H_5)_2$ | $CH_3$ | — | — | — | — | 8 | 162 |
| 57 | $CH_3$ | $CH_3$ | $\overset{O}{\underset{\|}{C}}-CH(C_2H_5)_2$ | — | — | $CH_3$ | — | — | 8 | 35 |
| 58 | $CH_3$ | $C_5H_{11}$ | $\overset{O}{\underset{\|}{C}}-CH_3$ | $CH_3$ | — | $CH_3$ | — | — | 8 | 45 |
| 59 | $CH_3$ | $C_5H_{11}$ | $\overset{O}{\underset{\|}{C}}-\underset{\underset{C_2H_5}{\|}}{CH}C_4H_9$ | $CH_3$ | — | $CH_3$ | — | — | 8 | 28 |
| 60 | $CH_3$ | $C_5H_{11}$ | $\overset{O}{\underset{\|}{C}}-C_5H_{11}$ | $CH_3$ | — | $CH_3$ | — | — | 8 | 38 |
| 61 | $CH_3$ | $C_5H_{11}$ | $\overset{O}{\underset{\|}{C}}-C_{15}H_{31}$ | $CH_3$ | — | $CH_3$ | — | — | 8 | 28 |
| 62 | $CH_3$ | $C_5H_{11}$ | $\overset{O}{\underset{\|}{C}}CH_3$ | $CH_3$ | — | — | — | — | 8 | 95 |
| 63 | $CH_3$ | $C_9H_{19}$ | $\overset{O}{\underset{\|}{C}}CH_3$ | $CH_3$ | — | — | — | — | 8 | 21 |
| 64 | $CH_3$ | $C_9H_{19}$ | $\overset{O}{\underset{\|}{C}}CH_3$ | $CH_3$ | — | $CH_3$ | — | — | 8 | 32 |
| 65 | $CH_3$ | $C_9H_{19}$ | $\overset{O}{\underset{\|}{C}}CH_3$ | CL | — | CL | — | — | 8 | 5 |
| 66 | $CH_3$ | $C_9H_{19}$ | $\overset{O}{\underset{\|}{C}}-CH\underset{C_2H_5}{\overset{C_4H_9}{<}}$ | $CH_3$ | — | — | — | — | 8 | 0 |

TABLE I-continued

| Example No. | R₁ | R₂ | Y | X₂ | X₃ | X₄ | X₅ | X₆ | RATE LBS/A | % INCREASE IN SUGAR |
|---|---|---|---|---|---|---|---|---|---|---|
| 67 | $CH_3$ | $C_9H_{19}$ | $\underset{C_2H_5}{\overset{O}{\underset{\|}{C}}-CH\overset{C_4H_9}{\diagup}}$ | CL | — | CL | — | — | 8 | 0 |
| 68 | $CH_3$ | $C_9H_{19}$ | $\underset{C_2H_5}{\overset{O}{\underset{\|}{C}}-CH\overset{C_4H_9}{\diagup}}$ | $CH_3$ | — | $CH_3$ | — | — | 8 | 0 |
| 69 | $CH_3$ | $C_5H_{11}$ | $\underset{C_2H_5}{\overset{O}{\underset{\|}{C}}-CH\overset{C_4H_9}{\diagup}}$ | $CH_3$ | — | — | — | — | 8 | 0 |
| 70 | $CH_3$ | $C_9H_{19}$ | $\overset{O}{\underset{\|}{C}}C_5H_{11}$ | $CH_3$ | — | $CH_3$ | — | — | 8 | 10 |
| 71 | $CH_3$ | $C_9H_{19}$ | $\overset{O}{\underset{\|}{C}}C_5H_{11}$ | $CH_3$ | — | — | — | — | 8 | 0 |
| 72 | $CH_3$ | $C_5H_{11}$ | $\overset{O}{\underset{\|}{C}}C_5H_{11}$ | — | — | — | — | — | 8 | 22 |
| 73 | $CH_3$ | $C_9H_{19}$ | $\overset{O}{\underset{\|}{C}}C_{15}H_{31}$ | CL | — | CL | — | — | 8 | 10 |
| 74 | $CH_3$ | $C_9H_{19}$ | $\overset{O}{\underset{\|}{C}}-C_{15}H_{31}$ | $CH_3$ | — | $CH_3$ | — | — | 8 | 0 |
| 75 | $CH_3$ | $C_9H_{19}$ | $\overset{O}{\underset{\|}{C}}-C_{15}H_{31}$ | $CH_3$ | — | — | — | — | 8 | 25 |
| 76 | $CH_3$ | $C_5H_{11}$ | $\overset{O}{\underset{\|}{C}}C_{15}H_{31}$ | $CH_3$ | — | — | — | — | 8 | 0 |
| 77 | $CH_3$ | $CH_3$ | $\overset{O}{\underset{\|}{C}}-CH_3$ | CL | CL | $CH_3$ | — | — | 8 | 0 |
| 78 | $CH_3$ | $CH_3$ | $\underset{C_2H_5}{\overset{O}{\underset{\|}{C}}CH\overset{C_4H_9}{\diagup}}$ | CL | CL | $CH_3$ | — | — | 8 | 0 |
| 79 | $CH_3$ | $CH_3$ | $\overset{O}{\underset{\|}{C}}C_7H_{15}$ | CL | CL | $CH_3$ | — | — | 8 | 0 |
| 80 | $CH_3$ | $CH_3$ | $\overset{O}{\underset{\|}{C}}CH(CH_3)_2$ | CL | CL | $CH_3$ | — | — | 8 | 0 |
| 81 | $CH_3$ | $CH_3$ | $\overset{O}{\underset{\|}{C}}C_{17}H_{35}$ | $CH_3$ | — | — | — | — | 8 | 35 |
| 82 | $-CH\overset{CH_3}{\underset{CH_3}{\diagup}}$ | | $\overset{O}{\underset{\|}{C}}CH_3$ | $CH_3$ | — | $CH_3$ | — | — | 8 | 369 |
| 83 | $-CH\overset{CH_3}{\underset{CH_3}{\diagup}}$ | | $\overset{O}{\underset{\|}{C}}C_5H_{11}$ | $CH_3$ | — | $CH_3$ | — | $CH_3$ | 8 | 306 |

TABLE I-continued

| Example No. | R₁ | R₂ | Y | X₂ | X₃ | X₄ | X₅ | X₆ | RATE LBS/A | % INCREASE IN SUGAR |
|---|---|---|---|---|---|---|---|---|---|---|
| 84 | —CH(CH₃)₂ | | —C(O)—C₆H₃(Cl)(Cl) (3,4-dichlorobenzoyl) | CH₃ | | CH₃ | — | CH₃ | 8 | 156 |
| 85 | —CH(CH₃)₂ | | —C(O)CH(C₄H₉)(C₂H₅) | CH₃ | | CH₃ | — | CH₃ | 8 | 131 |
| 86 | CH₃ | CH₃ | —C(O)CH₃ | —OCH₃ | | — | — | — | 8 | 0 |
| 87 | CH₃ | CH₃ | —C(O)C₅H₁₁ | —OCH₃ | | — | — | — | 8 | 25 |
| 88 | C₂H₅ | | —C(O)—CH(C₄H₉)(C₂H₅) | CH₃ | | CH₃ | — | CH₃ | 8 | 124 |
| 89 | C₃H₇ | | —C(O)CH₃ | CH₃ | | — | — | — | 8 | 196 |
| 90 | CH₃ | — | —C(O)—CH₃ | CH₃ | — | CH₃ | — | CH₃ | 8 | 167 |
| 91 | CH₃ | — | —C(O)—CH₃ | CL | CL | CH₃ | — | — | 8 | 0 |
| 92 | CH₃ | | —C(O)—C₅H₁₁ | CL | CL | CH₃ | — | — | 8 | 0 |
| 93 | CH₃ | | —C(O)—C₅H₁₁ | CH₃ | — | CH₃ | — | CH₃ | 8 | 67 |
| 94 | CH₃ | | —C(O)—CH₃ | CL | — | CL | — | — | 8 | 62 |
| 95 | CH₃ | | —C(O)—C₅H₁₁ | CL | — | CL | — | — | 8 | 119 |
| 96 | —CH(CH₃)₂ | | —C(O)—CH₃ | CH₃ | | CH | — | — | 8 | 246 |
| 97 | —CH(CH₃)₂ | | —C(O)C₅H₁₁ | CH₃ | | CH₃ | — | — | 8 | 208 |
| 98 | —CH(CH₃)₂ | | CCHC₄H₉(C₂H₅) | CH | | CH | — | — | 4 | 175 |
| 99 | C₃H₇ | | —C(O)C₅H₁₁ | CH₃ | — | — | — | — | 8 | 167 |
| 100 | CH(CH₃)₂ | | —C(O)CH(C₄H₉)(C₂H₅) | CH₂ | — | — | — | — | 8 | 159 |

TABLE I-continued

| Example No. | $R_1$ | $R_2$ | Y | $X_2$ | $X_3$ | $X_4$ | $X_5$ | $X_6$ | RATE LBS/A | % INCREASE IN SUGAR |
|---|---|---|---|---|---|---|---|---|---|---|
| 101 | $C_2H_5$ | | $\overset{O}{\underset{\|}{C}}CH_3$ | $CH_3$ | — | — | — | — | 8 | 220 |
| 102 | $C_2H_5$ | | $\overset{O}{\underset{\|}{C}}C_5H_{11}$ | $CH_3$ | — | — | — | — | 8 | 267 |
| 103 | $-\langle S \rangle$ | | $\overset{O}{\underset{\|}{C}}CH_3$ | $CH_3$ | — | $CH_3$ | — | $CH_3$ | 8 | 197 |
| 104 | $CH_3$ | $CH_3$ | $\overset{O}{\underset{\|}{C}}CH(C_4H_9)(C_2H_5)$ | — | $CH_3$ | — | — | — | 8 | — |
| 105 | $C(CH_3)_3$ | | $\overset{O}{\underset{\|}{C}}C_5H_{11}$ | $CH_3$ | — | $CH_3$ | — | — | .25 | 33 |
| 106 | $CH(CH_3)_2$ | | $\overset{O}{\underset{\|}{C}}C_5H_{11}$ | $CH_3$ | — | $CH_3$ | — | — | 8 | 255 |
| 107 | $CH(CH_3)_2$ | | $\overset{O}{\underset{\|}{C}}C_2H_5$ | $CH_3$ | | $CH_3$ | — | — | 8 | 347 |
| 108 | $CH_3$ | $CH_3$ | $\overset{O}{\underset{\|}{C}}C=C(CH_3)_2$ | $CH_3$ | — | — | — | — | 8 | 347 |
| 109 | $CH(CH_3)_3$ | | $\overset{O}{\underset{\|}{C}}C_2H_5$ | $CH_3$ | — | $CH_3$ | — | $CH_3$ | .25 | 2 |
| 110 | $C(CH_3)_2$ | | $\overset{O}{\underset{\|}{C}}C_2H_5$ | $CH_3$ | — | $CH_3$ | — | — | .25 | 28 |
| 111 | $CH(CH_3)_2$ | | $\overset{O}{\underset{\|}{C}}C_2H_5$ | $C_2H_5$ | — | — | — | — | .50 | 36 |
| 112 | $CH(CH_3)_2$ | | $\overset{O}{\underset{\|}{C}}C_5H_{11}$ | $C_2H_5$ | — | — | — | — | .25 | 59 |
| 113 | $CH(CH_3)_2$ | | $\overset{O}{\underset{\|}{C}}C_2H_5$ | $CH_3$ | — | $CH_3$ | — | $CH_3$ | .50 | 108 |
| 114 | $CH(CH_3)_2$ | | $\overset{O}{\underset{\|}{C}}C_3H_7$ | $CH_3$ | — | $CH_3$ | — | $CH_3$ | .25 | 16 |
| 115 | $CH(CH_3)_2$ | | $\overset{O}{\underset{\|}{C}}CH(CH_3)_2$ | $CH_3$ | | $CH_3$ | — | $CH_3$ | .25 | 13 |
| 116 | $CH(CH_3)_2$ | | $\overset{O}{\underset{\|}{C}}C_7H_{15}$ | $CH_3$ | | $CH_3$ | — | $CH_3$ | .50 | 21 |
| 117 | $CH(CH_3)_2$ | | $\overset{O}{\underset{\|}{C}}C_4H_9$ | $CH_3$ | | $CH_3$ | — | $CH_3$ | .50 | 87 |
| 118 | $-CH_3$ | $-CH_3$ | Na | CL | | CL | — | — | 2 | 6 |
| 119 | $-CH_3$ | $-CH_3$ | Na | $CH_3$ | | $CH_3$ | — | — | 1 | 21 |
| 120 | $-CH_3$ | $-CH_3$ | $-C_2H_5OCH_3$ | $CH_3$ | | $CH_3$ | — | — | 1 | 20 |
| 121 | $-CH_3$ | | $-CH_2OCH_3$ | $CH_3$ | | $CH_3$ | — | — | 8 | 147 |
| 122 | $-CH_3$ | $-CH_3$ | $-C_{12}H_{13}$ | — | | — | — | — | 8 | 24 |
| 123 | $-CH_3$ | $-CH_3$ | $-CH_2-CH(CH_3)_2$ | — | | — | — | — | 8 | 7 |

EXAMPLES 124 to 145

Several of the compounds listed in Table I were applied to high sucrose sorghum (variety-Ramada) at the four (4) leaf stage of growth at the rate of one (1) pound of compound per acre. Application was made by spraying 10 ml. of an aqueous solution of each perpendicular compound upon 6"×10" market packs of sorghum at a volume of 200 gallons per acre. The solutions were preared by dissolving each compound in acetone and diluting the resulting solution with water to a final volume of 10 ml.

The sorghum was harvested ten days after each treatment. The sap of each stalk was then analyzed for brix by means of a refractometer for sugar content. The average increase in sugar content observed using each compound from 4 samples employed is set forth in Table II on a dry weight basis as compared to an untreated control.

Table II presents percent increases in sugar content, measured on a dry weight basis, using each compound, as compared to an untreated control sample. The sample comprised from about 10 to about 12 stalks each, and measurements were made by cutting and weighing the samples, and then air drying them in a forced convection oven at 94° F. for 48 hours prior to reweighing, providing increases in sugar expressed on a dry weight basis.

The results are presented in Table II which follows:

TABLE II

| Example No. | Compound from Table I Example No. | % Increase in Sugar (Dry Wt. Basis) Using Compound as Compared to an Untreated Control Sample |
|---|---|---|
| 124 | 4 | 27 |
| 125 | 5 | 39 |
| 126 | 9 | 0 |
| 127 | 10 | 4 |
| 128 | 11 | 25 |
| 129 | 119 | 21 |
| 130 | 14 | 4 |
| 131 | 16 | 44 |
| 132 | 19 | 24 |
| 133 | 25 | 10 |
| 134 | 26 | 38 |
| 135 | 27 | 21 |
| 136 | 64 | 25 |
| 137 | 121 | 0 |
| 138 | 72 | 0 |
| 139 | 73 | 17 |
| 140 | 75 | 13 |
| 141 | 76 | 2 |
| 142 | 81 | 16 |
| 143 | 90 | 14 |
| 144 | 96 | 92 |
| 145 | 97 | 100 |

EXAMPLES 146 and 147

Two of the compounds listed in Table I above were applied to sugar cane plants (variety CP65-357) at the rate 4 ounces of compound per acre. Plants were seleted for testing that had at least 8 to 10 mature internodes. Solutions of each compound were prepared by dissolving the compound in acetone and diluting the solution with water. The solution of compound was applied to the test plant, by means of a syringe, onto the spindle area at the top of the last visible dewlap of 3 stalks. Each stalk was treated with 0.6 ml. of solution containing 4 mg. of the respective compound.

The above procedure was repeated for each compound at rates of 8 and 16 ounces of compound per acre. In this instance, 3 plant stems were treated with 0.6 ml. quantities of a solution containing 8 and 16 mg. of each compound, respectively.

Three weeks after treatment, the stems were harvested in the following manner. The first (the uppermost) internode and the fifth internode for each stems was removed and analyzed for brix by means of a refractometer and for reducing sugars using Benedict's copper reduction reaction. Sucrose content was then calculated from the difference between these values. The average results obtained for each compound employed at application rates of 4, 8, and 16 ounces of compound per acre, respectively, were measured and compared against a control of untreated sugar cane. The results, in terms of average percent sucrose content and in terms of percent sucrose increase as compared to the control, as given for both the first and fifth internode are presented in Table III which follows:

TABLE III

| Example No. | Compound from Table I Example No. | Rate of Application Ounces/Acre | 1st Internode | | 5th Internode | |
|---|---|---|---|---|---|---|
| | | | % Sucrose | % Increase | % Sucrose | % Increase |
| 146 | 97 | 4 | 18.0 | 48 | 22.3 | 21 |
| | | 8 | 17.8 | 46 | 23.9 | 30 |
| | | 16 | 11.2 | −8 | 22.1 | 20 |
| 147 | 83 | 4 | 16.3 | 34 | 23.1 | 26 |
| | | 8 | 15.7 | 29 | 22.9 | 24 |
| | | 16 | 12.8 | 5 | 21.1 | 15 |
| Control Example | None | | 12.2 | — | 18.4 | — |

What is claimed is:

1. A method for increasing the sugar content of plants which comprises applying to such plants prior to harvesting an effective amount of a compound of the formula:

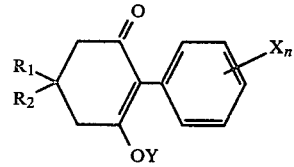

wherein:
$R_1$ is a hydrogen atom or an alkyl group having from 1 to 4 carbon atoms,
$R_2$ is a hydrogen atom, an alkyl group having from 1 to 10 carbon atoms, or a cycloalkyl group having from 5 to 10 carbon atoms.
Y is a hydrogen atom, an alkanoyl, alkynol, aryoyl or alkanoyl group having from 6 to 12 carbon atoms or a cation selected from the group consisting of ammonium radicals, alkaline metal cations and alkaline earth metal cations.
X is an alkyl group having from 1 to 4 carbon atoms, an alkoxy group having from 1 to 4 carbon atoms, a halogen atom, a nitro group, an amino group, or a cyano group.
n is an integer of 1 to 3.

2. The method of claim 1 wherein the compound is the 3-alkanoyloxy-5-isopropyl-2-(2,4-dimethylphenyl)-

2-cyclohexen-1-one wherein the alkenoyloxy group has from 2 to 12 carbons.

3. The method of claim 1 wherein the compound is the 3-alkanoyloxy-5-isopropyl-2-(2,4,6-trimethylphenyl)-2-cyclohexen-1-one wherein the alkenoyloxy group has from 2 to 12 carbons.

4. The method of claim 1 wherein the compound is applied to said plants at a time of from about 1 to about 7 weeks prior to harvesting.

5. The method of claim 1 wherein application of the compound to said plant is made at a rate of from about ⅛ lb./acre to about 8 lbs./acre.

6. The method of claim 1 wherein application of the compound to said plant is made at a rate of from about ¼ lb./acre to about 2 lb./acre.

7. The method of claim 1 wherein application of the compound to the plant is made at a rate of from about ¼ lb./acre to about 1 lb./acre.

8. The method of claim 1 wherein the plants are sugar cane.

9. The method of claim 1 wherein said plants are sorghum plants.

10. The method of claim 1 wherein application of the compond to said plant is made from about 3 to about 5 weeks prior to harvesting.

* * * * *

UNITED STATES PATENT AND TRADEMARK OFFICE
CERTIFICATE OF CORRECTION

PATENT NO. : 4,351,666
DATED : September 28, 1982
INVENTOR(S) : J.F. Koerwer

It is certified that error appears in the above—identified patent and that said Letters Patent is hereby corrected as shown below:

Column 20: line 58, before the word "group", delete "alkanoyl", insert -- alkenoyl --.

Signed and Sealed this

First Day of March 1983

[SEAL]

Attest:

GERALD J. MOSSINGHOFF

*Attesting Officer*    *Commissioner of Patents and Trademarks*